United States Patent [19]

Harendza-Harinxma

[11] 4,217,222

[45] Aug. 12, 1980

[54] APPARATUS FOR PROCESSING MUNICIPAL SOLID WASTE AND SEWAGE SLUDGE

[76] Inventor: Alfred J. Harendza-Harinxma, 50 Merion Pl., Lawrenceville, N.J. 08648

[21] Appl. No.: 779,689

[22] Filed: Mar. 21, 1977

[51] Int. Cl.² .............................................. B01D 35/00
[52] U.S. Cl. ................................. 210/177; 210/179; 210/180; 210/181; 210/182; 210/188; 210/199; 210/202
[58] Field of Search .............. 55/33, 59, 74; 110/8 P, 110/14; 202/100, 128, 129, 130, 131, 132, 249; 210/10, 63 R, 67, 71, 152, 177, 179, 180, 181, 182, 188, 199, 201, 202, 218, 219, 220

[56] References Cited

U.S. PATENT DOCUMENTS

| | | | |
|---|---|---|---|
| 3,152,796 | 10/1964 | Ramstack, Jr. | 110/14 |
| 3,549,010 | 12/1970 | Marsh et al. | 210/71 |
| 3,638,399 | 12/1972 | Walker | 55/59 |
| 3,652,405 | 3/1972 | Hess et al. | 210/71 X |
| 3,794,565 | 2/1974 | Bielski et al. | 202/131 X |
| 3,887,461 | 6/1975 | Nickerson et al. | 210/71 X |
| 3,938,449 | 2/1976 | Frisz et al. | 110/14 X |
| 3,954,605 | 5/1976 | Davies et al. | 210/71 X |
| 3,963,471 | 6/1976 | Hampton | 210/10 X |
| 4,010,098 | 3/1977 | Fassell | 210/67 X |

*Primary Examiner*—Robert H. Spitzer

[57] ABSTRACT

Sewage sludge and municipal solid waste are simultaneously processed by first dissolving a catalyst, such as sodium aluminate, in the sludge, then mixing the sludge-aluminate mixture with the municipal waste to form a carbonizing mixture. After dewatering and drying, the mixture is carbonized in a furnace heated by a mixture of city gas and pyrolysis gases given off by the furnace.

1 Claim, 6 Drawing Figures

APPARATUS FOR PROCESSING MUNICIPAL SOLID WASTE AND SEWAGE SLUDGE

BACKGROUND OF THE INVENTION

1. Field of the Invention

Broadly speaking, this invention relates to apparatus for carbonizing a substance containing cellulose and other organics. More particularly; in a preferred embodiment, this invention relates to apparatus for carbonizing cellulose and other organics—containing waste products with an alkali metal aluminate which has been dissolved in sewage sludge containing from 4–15% solid material, e.g. human faeces.

2. Discussion of the Prior Art

My U.S. Pat. No. 3,961,025, which issued June 1, 1976, discloses a method of treating municipal solid waste (MSW), e.g. raw refuse such as domestic rubbish and garbage, by combining the waste with an alkali metal meta-aluminate, such as sodium aluminate, to form a carbonizing mixture and then heating the mixture in a furnace to carbonize the waste material.

My co-pending U.S. patent application Ser. No. 729,890, filed on Oct. 6, 1976, now U.S. Pat. No. 4,111,800 discloses an improvement over my earlier patent wherein the municipal solid waste is carbonized by first treating it with an alkali metal aluminate, such as sodium aluminate, which has been dissolved in sewage sludge containing from 4–15% solid material, such as human faeces.

The problem, of course, is to devise an efficient, safe and relatively inexpensive plant to practice the above process. Fortunately, the above problem has been solved by the invention disclosed and claimed herein.

SUMMARY OF THE INVENTION

In a preferred embodiment my invention comprises apparatus for carbonizing cellulose and other organics—containing municipal solid waste products with an alkali metal aluminate which has been disolved in sewage sludge. The apparatus comprises means for mixing filtered, condensed to about 15% of solids sewage sludge with a water solution of alkali metal aluminate, means for mixing the sludge—alkali metal aluminate mixture with shredded municipal solid waste, means for removing the moisture from said municipal solid waste/sludge—alkali metal aluminate mixture and means for heating the dried municipal solid waste/sludge—alkali metal aluminate mixture to a temperature sufficient to carbonize the same.

DETAILED DESCRIPTION OF THE INVENTION

The apparatus to be discussed is merely illustrative of the many configurations that can be realized to practice my invention. The previously referenced U.S. Pat. No. 3,961,025 and co-pending U.S. Pat. application Ser. No 729,890, filed on Oct. 6, 1976, now U.S. Pat. No. 4,111,800 are hereby incorporated by reference as if they were fully set forth herein.

Figure 6:
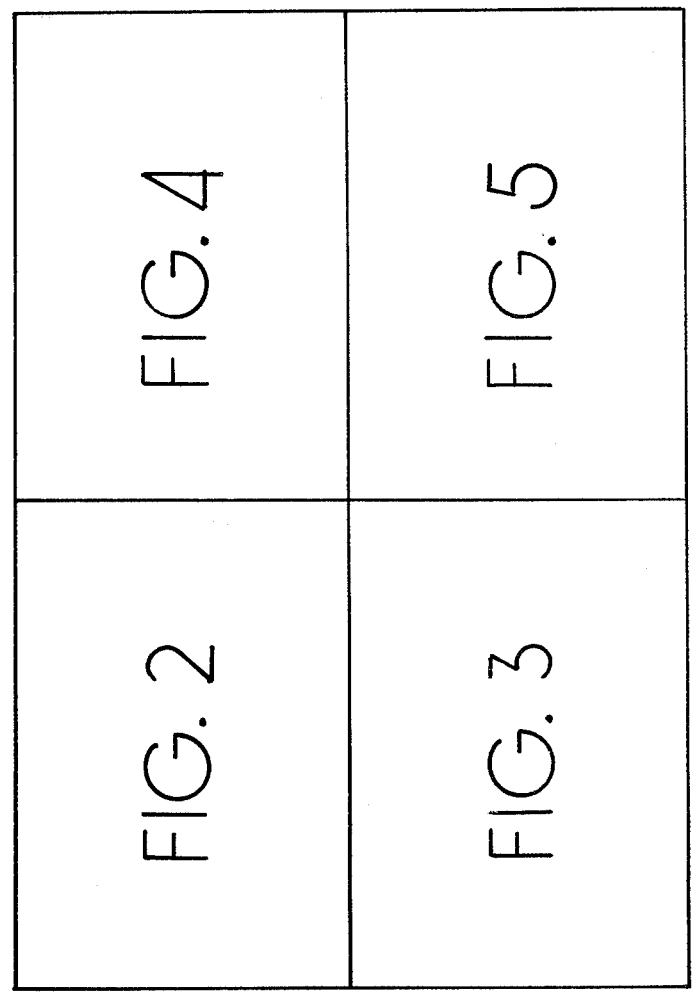
FIG. 6 is a diagram showing how FIGS. 2–5 may be assembled into a single composite drawing.

FIGS. 2–5 of the drawing may be assembled as shown in FIG. 6 to form a composite drawing of the apparatus. As shown, the incoming sewage sludge is fed through a pipe 10 to a filter 11 to remove excess water. The dewatering raises the solids content up to 20%. Thence it is pumped into a sludge-holding tank 12 by a pump 13. A stirrer 14 actuated by a motor 16 keeps the sludge in motion to prevent settling. Although not shown in the drawing, the incoming sludge will in general be treated prior to filtration in filter 11. For example, the inorganic solids, such as sand in the sludge may be cut-up to prevent damage to the pumps; the cut-up sewage may be pumped into a Parshall flume and grit chamber to remove sand, grit or other abrasive particles. The mixture may then be flowed into primary clarifier—biofilter and secondary clarifier to remove solids and the effluent treated with chlorine etc. to kill bacteria; however, all such sewage treatment is well known and forms no part of my invention.

Suffice it to say that, the sludge that enters into tank 12 will contain from 4.5% to 20% of solid waste. A water solution of sodium aluminate is fed through a pipe 17 into a pair of tanks 18—18 each of which is equipped with a stirrer 19 driven by a motor 21. The strength of the solium aluminate in tanks 18 can vary from 1% to saturation.

The sludge in tank 12 is then pumped by a pump 22 into a heated mixing chamber 23 which also receives the appropriate quantity of sodium aluminate solution from tanks 18 via a pump 24. Mixing chamber 23 also includes a stirrer 26 driven by a motor 27. Advantageously, chamber 23 is heated by a steam jacket 9 supplied by steam from a steam generator 28 (FIG. 5) via a steam inlet pipe 29. Spent steam is re-circulated back to generator 28 via a pipe 31.

Figure 3:
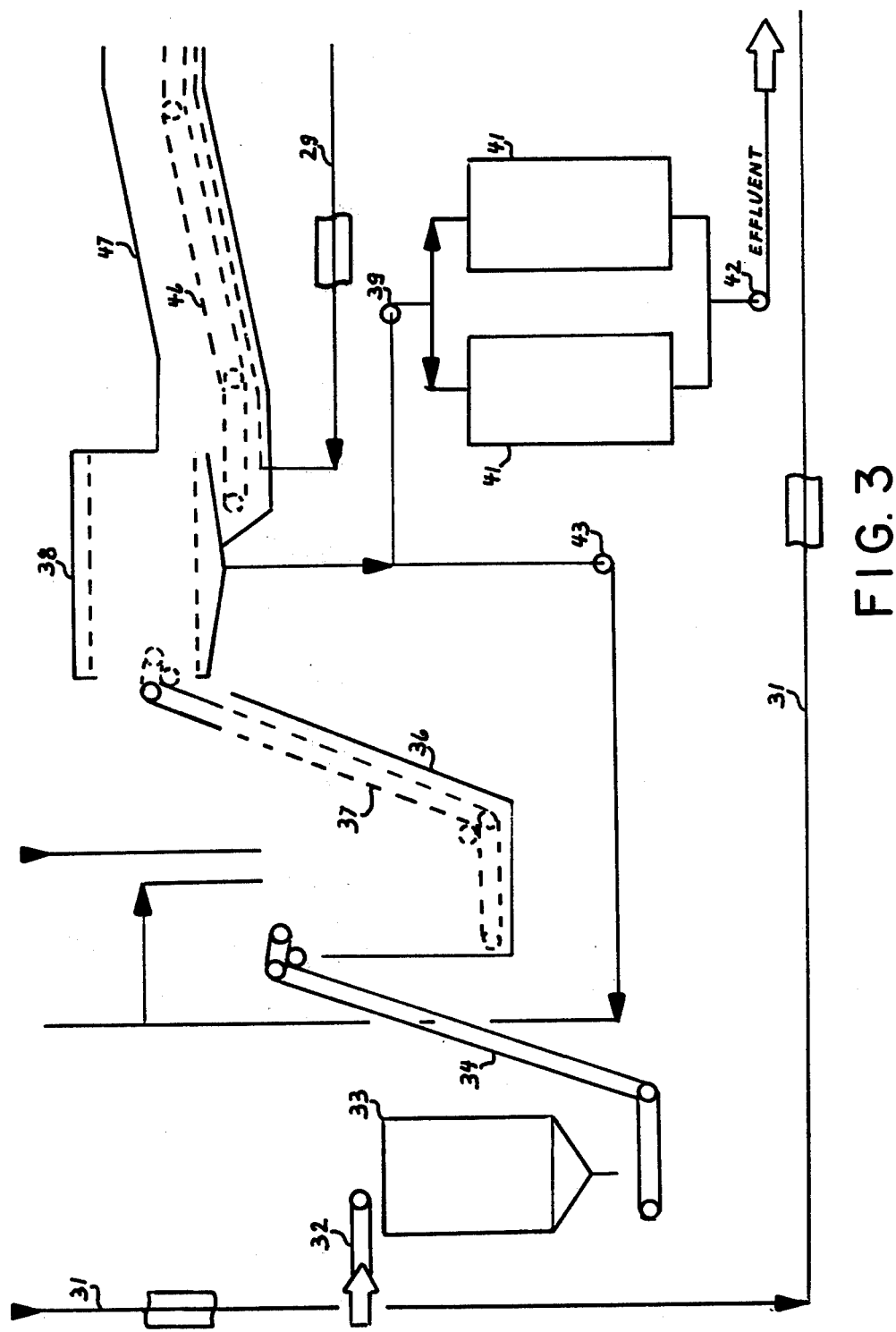
FIG. 3 is a more detailed drawing of the lower left-hand portion of FIG. 1 showing the apparatus used to shred or chop the incoming municipal solid waste and mix it with the mixture of sludge and sodium aluminate.

Turning now to FIG. 3, the incoming municipal solid waste is first dumped into a storage tank (not shown) then it is transported, via a conveyer belt 32 into a chopper or shredder 33, which cuts the refuse up into small pieces.

Although not shown in the drawing, conventional equipment may now be used to separate out the ferrous and not-ferrous metals, glass, and organic waste. For example, magnetic separating means can be used to separate the ferrous metals and a rotary drum screen can be used to separate the glass and non-ferrous metals.

However, the separation of shredded or chopped metals and glass from the cellulose contained waste is optional and may occur after the carbonization process.

Figure 1:
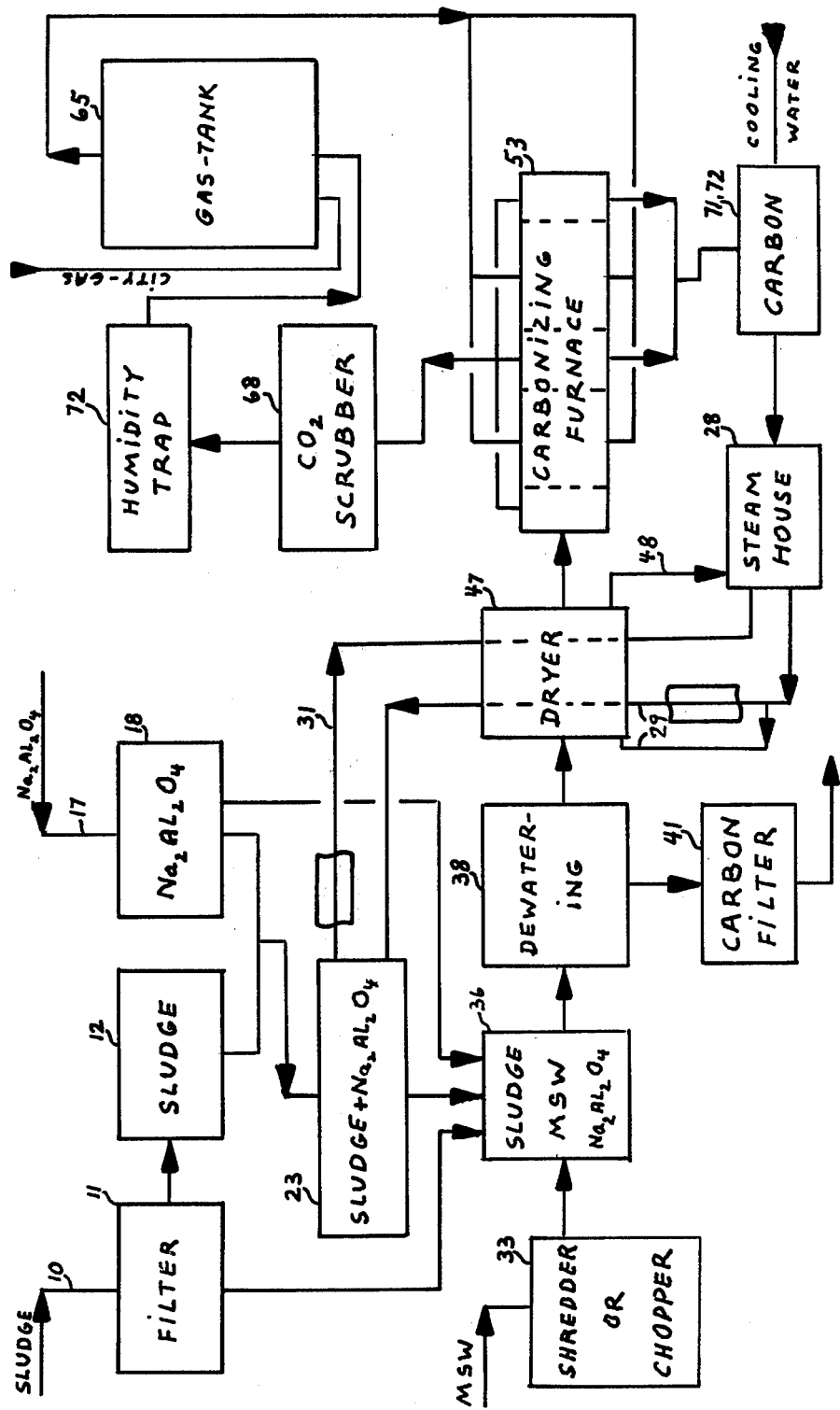
FIG. 1 is a block schematic drawing of the overall apparatus.
Figure 2:
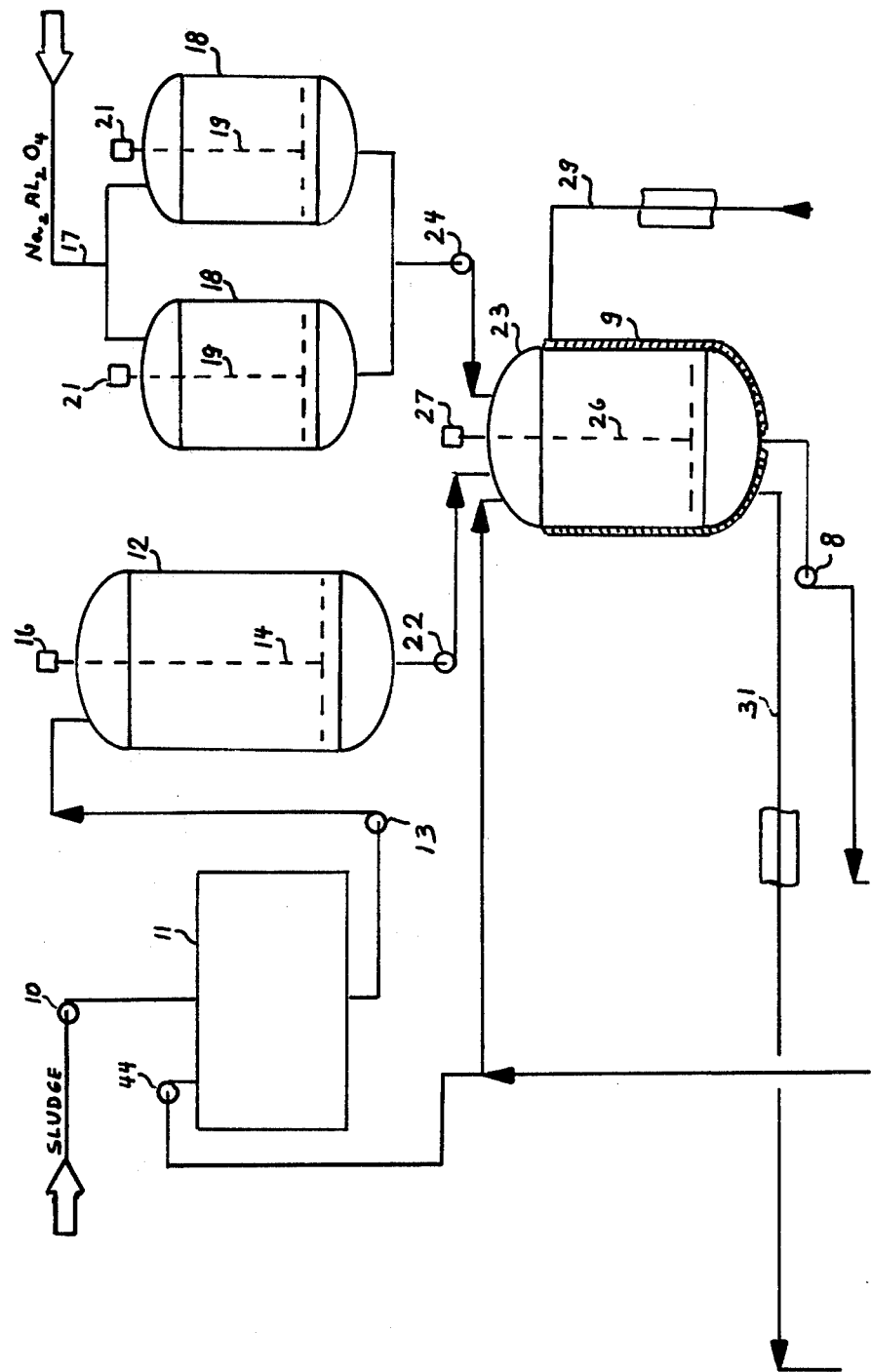
FIG. 2 is a more detailed drawing of the upper left-hand portion of FIG. 1 showing the apparatus used to mix the sewage sludge with the sodium aluminate.

After the non-cellulose containg products have been separated, the municipal solid waste is reduced to about 75% of its original weight. This remaining waste is then dropped into a second screw or belt conveyer 34 thence into a tank 36. Tank 36 also receives the sludge—aluminate mixture from tank 23, via a pump 8 (FIG. 2). The municipal solid waste and sludge—aluminate mixture are thoroughly mixed in chamber 36. The chamber 36 may be a tank with a stirrer or a pug mill.

The thoroughly mixed mixture is then fed via a screw or belt coveyer 37 into a dewatering chamber 38, for example a centrifugal acreened drum. The excess water removed from chamber 38 is pumped by a pump 39 through a plurality of carbon filters 41—41 then discharged as effluent by means of a pump 42 into a chlorine tank (not shown in the drawing). If desired, some of the excess water may be pumped by pump 43 into chambers 36 and 23 and by a pump 44 into filter 11.

The dewatered waste is discharged into a screw or belt conveyer 46 thence into a heated drying chamber 47. Hot air or steam may be used to heat chamber 47. In the drawing, steam is supplied from steam generator 28 via a pipe 29. Spent steam is re-circulated back to generator 28 via a pipe 48. The temperature within chamber 47 is about 120° C. The drying chamber may be a rotary drum or a stationary drying chamber with a conveyer belt 46.

The now dry or partly dry organic waste is fed into a chamber 51 having a continuously rotating screw 52 which forces the waste into the carbonizing chamber 53. The carbonizing chamber 53 comprises a rotatable carbon steel tube 54 within a metal drum 56. The drum 56 and the rotatable tube 54 are divided into 5 chambers separated from one another by four solid metal rims $57_1$ through $57_4$ that are welded on the inside drum.

Figure 4:
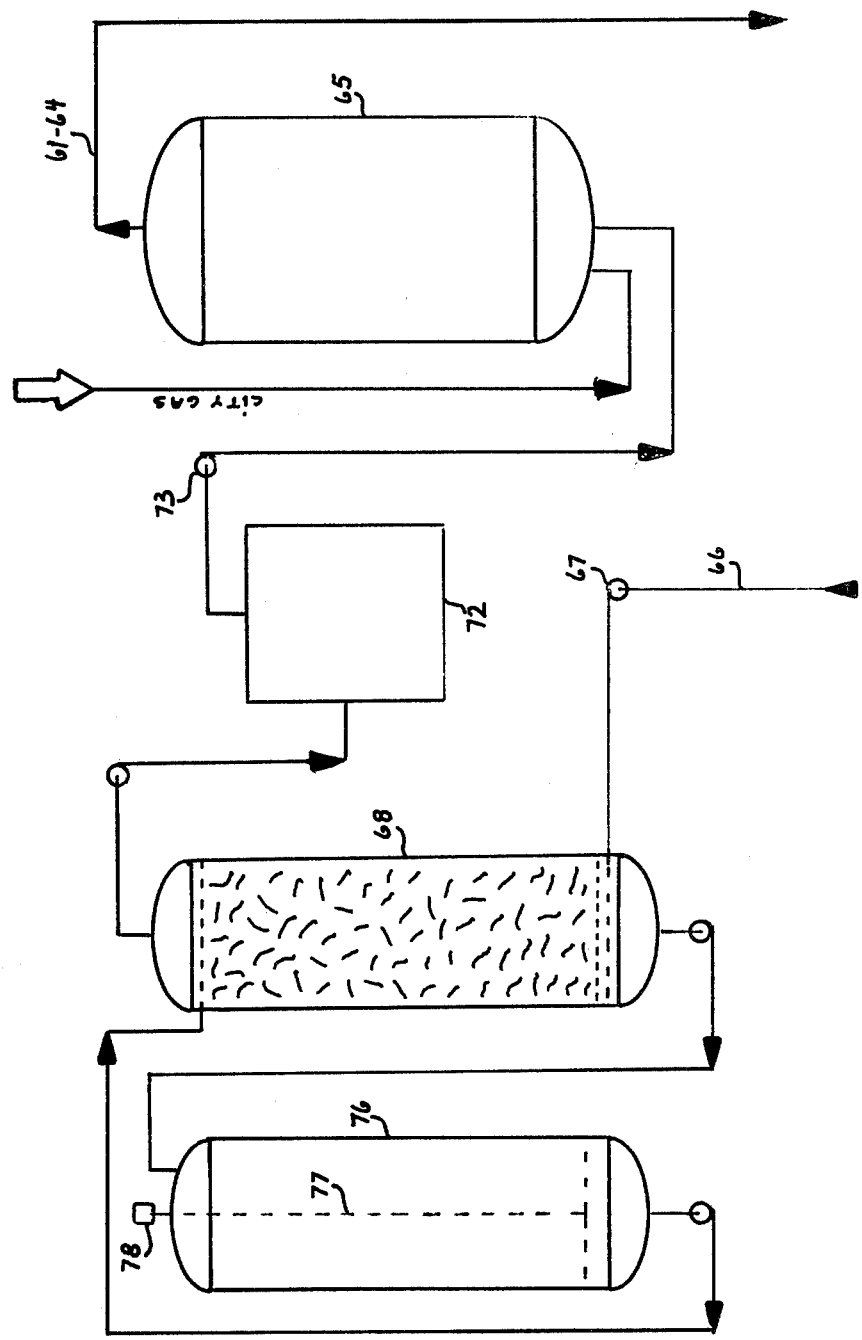
FIG. 4 is a more detailed drawing of the upper right-hand portion of FIG. 1 showing the apparatus used to store the gas required to heat the carbonizing furnace and to recycle the gases given off by the sludge and municipal solid waste as they are carbonized.
Figure 5:
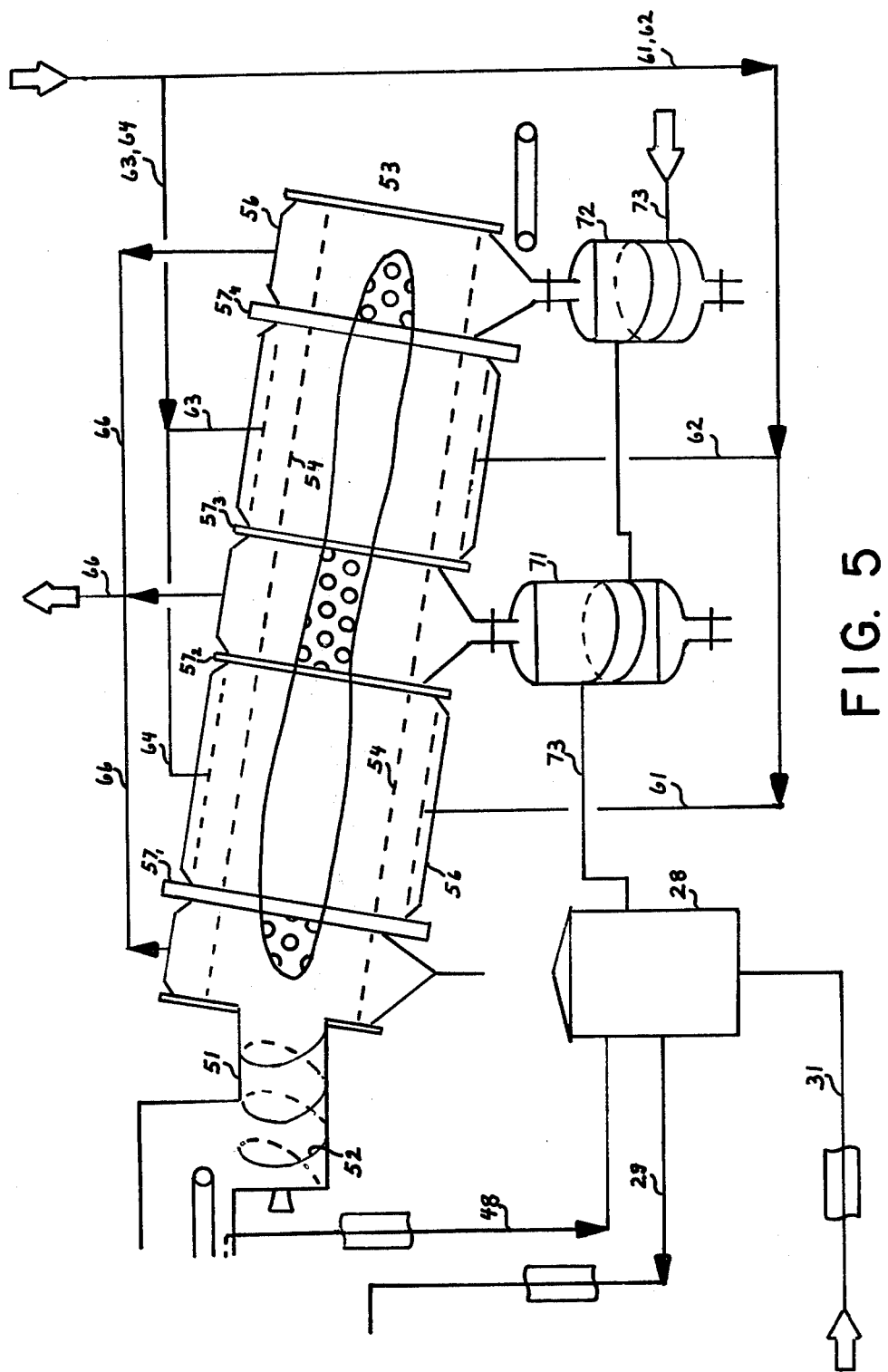
FIG. 5 is a more detailed drawing of the lower right-hand portion of FIG. 1 showing the apparatus used to carbonize the sludge and municipal solid waste mixture.

In chambers 1, 3 and 5 the walls of drum 54 are perforated for example by holes about ⅜" diameter, through which the pyrolysis gases and organic waste which has been carbonized can pass. The walls of the drum in chambers 2 and 4 are solid and it is here that the heating of the waste occurs, for example, by means of city gas supplied via lines 61 to 64 from gas tank 65 (FIG. 4).

The city gas is supplemented by the pyrolysis gases which are collected in chambers 1, 3 and 5. This pyrolysis gas is fed via line 66 and pump 67 to a $CO_2$-scrubber 68 thence, via a pump 71, to a freezing unit 72 which removes all remaining water. The dry, scrubbed gases are then pumped via a pump 73 into city gas tank 65. A tank 76, equipped with a stirrer 77 and motor 78, is filled with NaOH water solution and this is continuously re-circulated through $CO_2$-scrubber 68.

The organic material that has been converted into carbon leaves furnace 53 by way of the bottom of chambers 3 and 5. This is possible because furnace 53 is positioned at an angle of about 15° and rotates slowly so that the waste material that is input at the upper end of the furnace, moves slowly through the rotation of the drum in a helical path to the opposite end of the drum by means of a helix welded to the inside wall of the drum.

The carbonized material produced in my process is very brittle and easily pulverized during the rotation process and falls through the holes in the rotary drum and is collected in tanks 71 and 72. When it leaves the rotary drum the carbon is at a temperature of 225°–250° C. and is cooled by water from the city mains, via pipe 73. The water is thus heated and as preheated water is fed to the steam generator 28 to conserve energy. However, air also may be used to cool the carbon.

The apparatus shown is, of course, merely illustrative of many configurations that may be realized and all such variations are encompassed by the appended claims.

What I claim is:

1. Apparatus for carbonizing cellulose and other organic—containing municipal solid waste products with an alkali metal aluminate which has been dissolved in sewage sludge, which comprises:

means for shredding said municipal solid waste;
means, connected to said shredding means, for storing said shredded municipal solid waste;
means for storing said sewage sludge;
means for storing said liquid alkali metal aluminate;
means for mixing said sewage sludge with a water solution of an alkali metal aluminate;
means for connecting said sewage sludge storing means said liquid alkali metal aluminate storing means to said sewage sludge solution and alkali metal aluminate mixing means;
means for mixing said sewage sludge—alkali metal aluminate and said shredded municipal solid waste;
means for conducting the sewage sludge—alkali metal aluminate solution means to said mixing means for mixing said sewage sludge—alkali metal aluminate solution with shredded municipal solid waste;
means for removing the moisture from said municipal solid waste/sewage sludge—alkali metal aluminate mixture;
means for conducting the mixture of said sewage sludge—alkali metal aluminate—municipal solid waste to said means for removing the moisture from said municipal solid waste/sewage sludge—alkali metal aluminate mixture;
means for drying the dewatered municipal solid waste/sewage sludge—alkali metal aluminate mixture;
means for transporting the dewatered municipal solid waste/sewage sludge—alkali metal aluminate through said means for drying;
a carbonizing furance, said furnace being tilted at an angle of from 5° to 25° with the mixture to be carbonized entering at the upper end and flowing under the combination of gravitational and rotational forces towards the lower end, said furnace comprising:
a sealed cylindrical member;
a rotatable, cylindrical member concentrically and coaxially mounted within said sealed cylindrical stationary member;
means for rotating said rotatable member;
means for sealing the gap between the outer wall of said sealed cylindrical rotatable member and the inner wall of said stationary member, said sealing means dividing said furnace into first, second, third, fourth and fifth sub-chambers, the walls of said rotatable member being perforated in said first, third and fifth sub-chambers;
means for supplying a combustible gas to said second and fourth sub-chambers;
means for collecting pyrolysis gases from said first, third and fifth sub-chambers;
means, associated with said third and fifth sub-chambers, for collecting and cooling the carbonized material passing through the perforations in said rotatable chamber, said apparatus further comprising:
means, associated with said carbonizing furnace for collecting any pyrolysis gases given off by said mixture as it is carbonized;
means, connected to said collecting means, for scrubbing any $CO_2$ gas present in said pyrolysis gases;

means for connecting the pyrolysis gases collected by said collecting means to said $CO_2$ scrubbing means;

means, connected to said scrubbing means, for removing any excess moisture in said scrubbed pyrolysis gases;

means for connecting the scrubbed $CO_2$ gas to said moisture removing means;

means for adding said dried pyrolysis gases to the combustible gases in said gas supplying means to augment the heating of said heating means;

means for supplying a flow of cooling water;

means for discharging the carbonized material from the carbonizing furnace;

means for collecting and cooling the carbonized material discharged from said carbonizing furnace;

means for connecting said collecting and cooling means to said water supplying means;

means for generating steam, said generating means receiving the pre-heated output water flow from said collecting and cooling means, for supplying steam to said moisture-removing means and to said sewage sludge—alkali metal aluminate water solution mixing means;

means for feeding the dry mixture of municipal solid waste/sewage sludge—alkali metal aluminate into said rotary carbonizing furnace whereby said furnace heats said dried municipal solid waste/sewage sludge—alkali metal aluminate mixture to a temperature sufficient to carbonize the same.

* * * * *